United States Patent
Thomas

(10) Patent No.: US 7,122,038 B2
(45) Date of Patent: Oct. 17, 2006

(54) LOCALIZING DEVICE FOR VENTRICULOSTOMY

(76) Inventor: Jeffrey E. Thomas, 6101 Imperata St., NE., Apt. #1616, Albuquerque, NM (US) 87111

( * ) Notice: Subject to any disclaimer, the term of this patent is extended or adjusted under 35 U.S.C. 154(b) by 279 days.

(21) Appl. No.: 10/128,396

(22) Filed: Apr. 22, 2002

(65) Prior Publication Data

US 2003/0199886 A1    Oct. 23, 2003

(51) Int. Cl.
*A61B 19/00* (2006.01)
*A61B 1/06* (2006.01)

(52) U.S. Cl. ........................ 606/130; 600/429

(58) Field of Classification Search .......... 606/130, 606/1; 600/417, 429; 434/211, 214, 215, 434/284; 2/410, 6.2, 422, 448, 406, 209.13; D2/866, 895
See application file for complete search history.

(56) References Cited

U.S. PATENT DOCUMENTS

| | | | | |
|---|---|---|---|---|
| 1,776,175 A | * | 9/1930 | Wittekind | 446/27 |
| 3,345,752 A | * | 10/1967 | Gabriel | 33/456 |
| 3,514,787 A | * | 6/1970 | Kennedy, Jr. | 2/410 |
| 4,592,352 A | * | 6/1986 | Patil | 606/130 |
| 4,638,798 A | * | 1/1987 | Shelden et al. | 606/130 |
| 4,706,665 A | * | 11/1987 | Gouda | 606/130 |
| D319,240 S | * | 8/1991 | Caulder | D14/205 |
| 5,330,485 A | | 7/1994 | Clayman et al. | |
| 5,561,864 A | * | 10/1996 | DeMars | 2/209.13 |
| 5,601,570 A | * | 2/1997 | Altmann et al. | 606/130 |
| D387,191 S | * | 12/1997 | Berke | D2/891 |
| 6,000,065 A | * | 12/1999 | Deagan | 2/410 |
| 6,096,048 A | * | 8/2000 | Howard et al. | 606/130 |
| 6,206,885 B1 | | 3/2001 | Ghahremani et al. | |

OTHER PUBLICATIONS

International Search Report; PCT Serial No. PCT/US03/12404; Mailed Jan. 6, 2004.

* cited by examiner

*Primary Examiner*—Pedro Philogene
(74) *Attorney, Agent, or Firm*—Benesch, Friedlander, Coplan & Aronoff LLP

(57) ABSTRACT

A localizing apparatus includes a frame, a linear reference marker, and a target marker. The frame includes a first portion fixable to a first anatomical reference point. The linear reference marker is rotatable about the first anatomical reference point to align a second anatomical reference point with the first anatomical reference point. The target marker is rotatable about the first anatomical reference point to establish an angle from the linear reference marker such that the target marker is located in a desired plane.

18 Claims, 4 Drawing Sheets

LOCALIZING DEVICE FOR VENTRICULOSTOMY

FIELD OF THE INVENTION

The invention generally relates to locating devices. The invention finds particular application in medical devices referencing skull locations with respect to ventricles.

BACKGROUND OF THE DISCLOSURE

Most surgical neurological procedures require accurate placement of medical instruments within the patient's brain. A common neurological surgical procedure is a ventriculostomy in which a cerebral ventricle drain, shunt or catheter is implanted. The purpose of the drain or shunt (with or without a transducer or fiberoptic device) is to relieve high pressure cerebrospinal fluid (CSF) in a patient's cerebral ventricles resulting from congenital brain malformations, acute or chronic infections, tumors, intraventricular hemorrhage, normal pressure hydrocephalus or other intracranial space-occupying lesions, as well as to provide a reliable means to measure intracranial pressure or to deliver medication into the cerebrospinal fluid space.

Procedures for the placement of ventricular drains, shunts and catheters rely on the skill of the neurosurgeon. These procedures are often expensive and time consuming. After imaging the brain, the neurosurgeon forms a burr hole in the skull and guides a catheter through the burr hole toward landmarks on the ipsilateral or contralateral of the patient's head. The neurosurgeon must accurately conceptualize the internal topography of the brain during the procedure, and rely on this conceptualization to effectively place the catheter within the cerebral ventricle. In some procedures, the neurosurgeon checks the location of the catheter by imaging another CT scan of the brain following the operation. By verifying the position of the catheter within the brain, the neurosurgeon can effect longer shunt patency and decrease morbidity rates due to shunt malpositioning, as well as assure the accurate delivery of medication within the ventricle and the accurate measurement of intracranial pressure.

BRIEF SUMMARY OF THE INVENTION

A localizing apparatus includes a frame, a linear reference marker, and a target marker. The frame includes a first portion fixable to a first anatomical reference point. The linear reference marker is rotatable about the first anatomical reference point to align a second anatomical reference point with the first anatomical reference point. The target marker is rotatable about the first anatomical reference point to establish an angle from the linear reference marker such that the target marker is located in a desired plane.

Another aspect of the invention provides an apparatus to position instruments within a target. The apparatus includes a probe, a reference marker, and a target marker. The probe is configured to attach to a first reference point. The reference marker is configured to rotate about a center axis of the probe including an end configured to align a second reference point with the first reference point. The target marker is configured to rotate about the axis and to be positioned at an angle such that the target marker is located in a plane that transversely passes through the target.

Another aspect provides a localizing apparatus including a frame having a first and second end, an annular guide, a linear reference marker, and a linear target marker. The frame is configured to extend in an arc around a head and has an outer diameter surface and an inner diameter surface. The annular guide extends from the outer diameter surface to the inner diameter surface and is configured to direct the instrument toward the surface of the head. The first end of the frame is configured to fix the frame to a first anatomical reference point. The second end of the frame is configured to fix the frame to a second anatomical reference point. The linear reference marker is configured to rotate about the first end and to align a third anatomical reference point with the first anatomical reference point. The linear target marker is configured to rotate about the first end. The linear target marker is positioned at an angle from the linear reference marker such that the linear target marker is located in a plane that passes through the desired portion of the head.

Yet another aspect of the invention provides a method for localizing a portion of the brain. The method includes locating a first anatomical reference point, extending a first line from the first anatomical reference point to a second anatomical reference point such that the reference points are located in a sagittal plane, positioning a second line in the sagittal plane to pass through the first anatomical reference point at a determined angle from the first line such that the second line is oriented in a transverse plane that passes through the portion of the brain.

DETAILED DESCRIPTION OF A PREFERRED EMBODIMENT

Figures 1, 2:
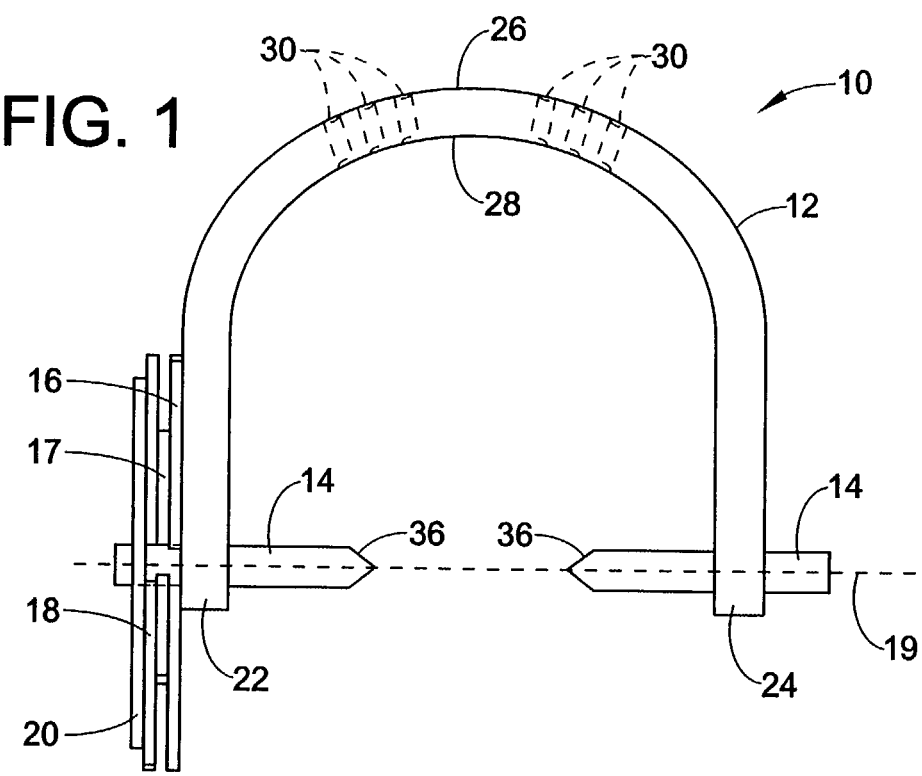
FIG. 1 is a schematic diagram of a first embodiment of a localizing device for ventriculostomy.
FIG. 2 is a lateral view of the first embodiment of FIG. 1 donned by a patient.

Referring now to the drawings, which are not intended to limit the invention but instead illustrate several exemplary embodiments, FIG. 1 illustrates a schematic of a localizing device 10 for ventriculostomy made in accordance with the teachings of the present invention. The localizing device 10 includes a U-shaped frame 12, probes 14, markers 16, 17 and 18, and a protractor 20. The probes 14 are threadedly received in the frame 12 and lie on an axis 19. The markers 16, 17 and 18, and the protractor 20 are rotatably attached to the frame 12 so that the markers 16, 17, 18 and protractor 20 may rotate about the axis 19. The frame 12 may also rotate about the axis 19. When the device 10 is donned by a patient, the probes 14 are fixed to the skull in the external auditory meati and the frame 12, anatomical reference marker 16, perpendicular reference marker 17, target marker 18, and protractor 20 may rotate about the axis 19.

The frame 12 is generally in the shape of an arc. The frame 12 includes a first end 22 and a second end 24. An outer surface 26 and an inner surface 28 of the frame 12 define the inner and outer arc lengths of the frame 12. In the embodiment shown in FIG. 1, the frame 12 is made of a member having a circular cross section. The frame 12, however, may have various cross sections without limiting functionality. The frame 12 is configured with an array of annular or other shaped guides 30 that extend from the outer surface 26 to the inner surface 28 of the frame 12. The guides 30 may extend perpendicular to the inner and outer surfaces 28 and 26 or may be angled to direct an instrument toward a specific region under the frame 12. By adjusting the angle and the lateral placement of the guides 30 on the frame 12, a neurosurgeon may choose alternative paths to the target.

The markers 16, 17, 18 are relatively positioned with respect to one of the probes 14 so that a neurosurgeon may reference certain anatomical points or planes as the portion of the brain is isolated for the ventriculostomy. The protractor 20 can be aligned with one of the markers 16, 17, or 18 such that angles can be measured between the markers 16, 17, or 18. When the markers 16, 17, 18 are properly positioned by the surgeon, then the frame 12 may be rotated to align the frame 12 with one of the markers 16, 17, 18.

The probes 14 are threadedly received in the frame 12 as is conventional in the art. The probes 14 may be advanced along the axis 19 toward one another and also retracted along the axis 19 by rotation relative to the frame 12. Contact surfaces 36 of the probes 14 are configured to contact an anatomical reference point, such as the external auditory meati, of the patient's head so that the frame 12, markers 16, 17, 18 and the protractor 20 may be fixed but for pivotal movement about the axis 19. The probes 14 may also fix the pivotal motion of the frame 12 so that the frame may not rotate about the axis 19. For example, a small hole may be positioned on the arc 12 to accommodate a locking screw. The locking screw is tightened down when the correct desired angulation of the arc 12 has been obtained, locking the arc in place with respect to the fixed probes 14. In an additional embodiment the EAM probes 14 may have prefixed accommodations, e.g. depressions, to provide easier locking down of the screw. Such a configuration allows a surgeon to use the fixed frame 12 to guide surgical tools during surgery.

FIG. 2 is a lateral view of the localizing device of FIG. 1 donned by a patient. The probes 14 are advanced on opposite sides of a patient's head 50 until the contact surfaces 36 (FIG. 1) of the probes contact a desired reference such as the external auditory meati. When the probes 14 are so positioned, the markers 16, 17, 18 and the protractor 20 are all centered for rotation about an axis normal to the external auditory meati. In this example, the external auditory meati serve as an anatomical reference point for localizing the portion of the brain. The markers 16, 17, 18 can be rotated about the anatomical reference point to align with other anatomical reference points and to define desired angles between the markers.

For example, the anatomical reference marker 16 may align the external auditory meati (centered on probe 14) with the most posterior point on the mandibular angle 21 (angulus mandibulae). The mandibular angle 21, the ipsilateral angle of the mandible when the jaw is closed, is a palpable anatomical reference point on the head (e.g. see FIG. 162: Eduard Pernkopf, Atlas of Topographical and Applied Human Anatomy, Volume I: Head and Neck. $2^{nd}$ Revised Edition. Urban & Schwarzenberg, Baltimore-Munich, 1980). After the anatomical reference marker 16 is aligned along this mandibulomeatal line (MML), the protractor 20 can reference angles with respect to the MML. Optionally, a perpendicular reference marker 17 may be aligned at 90° to the MML to create a perpendicular reference (angle θ). The target marker 18 may then be rotated to measure an angle from the perpendicular reference marker 17 (angle β) or the anatomical reference marker 16 (angle α) to mark a desired plane in which the target ventricle of the brain lies.

Alternatively, the markers 16, 17, 18 may be set in a fixed relative relationship so that a predetermined target portion of the ventricle is localized without the protractor 20. In this embodiment, when the anatomical reference marker 16 is aligned with the MML, the target marker 18 aligns with the plane that transversely intersects the target portion of the brain.

Figure 3:
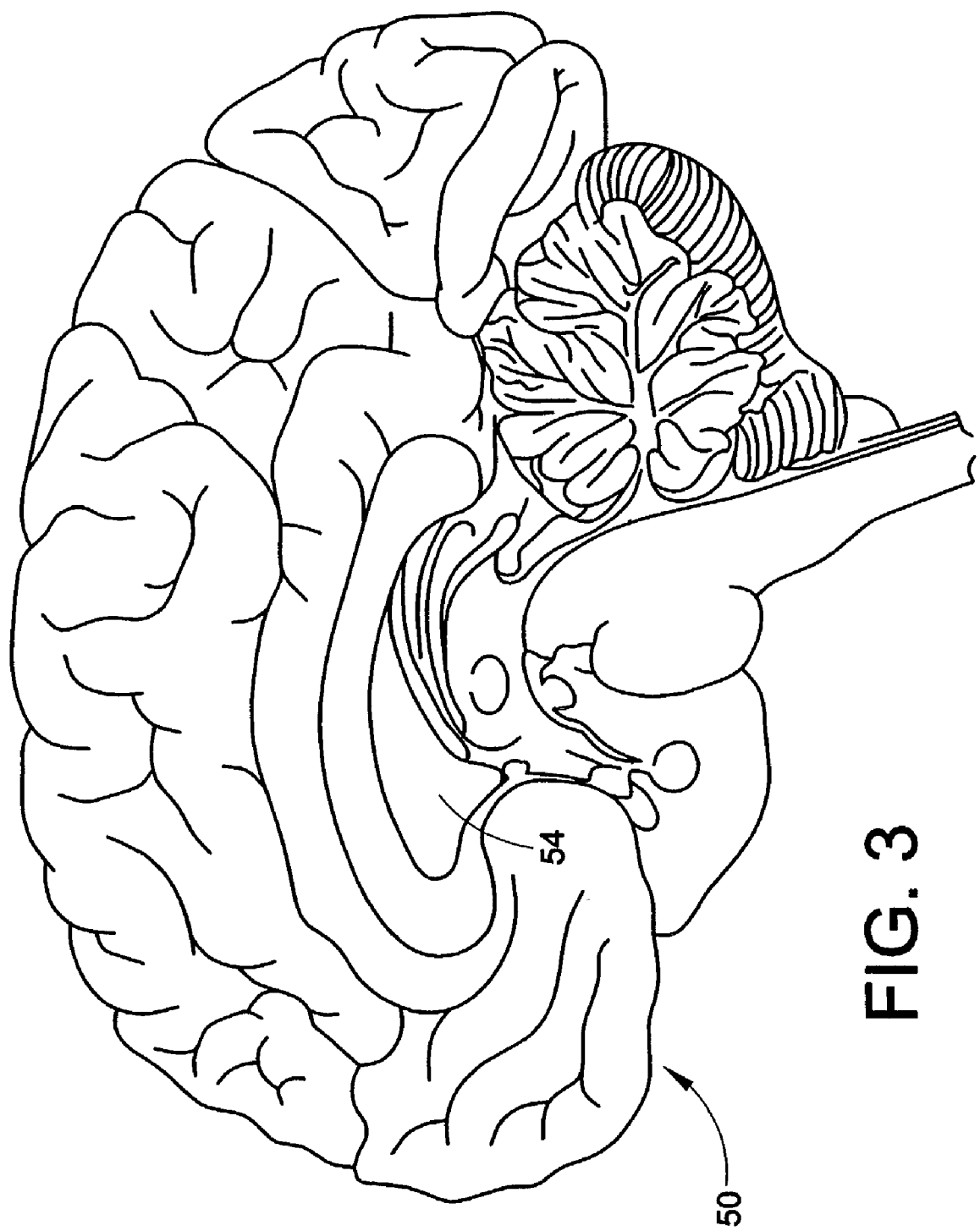
FIG. 3 is a schematic diagram of a sagittal scan of a brain.
Figure 4:
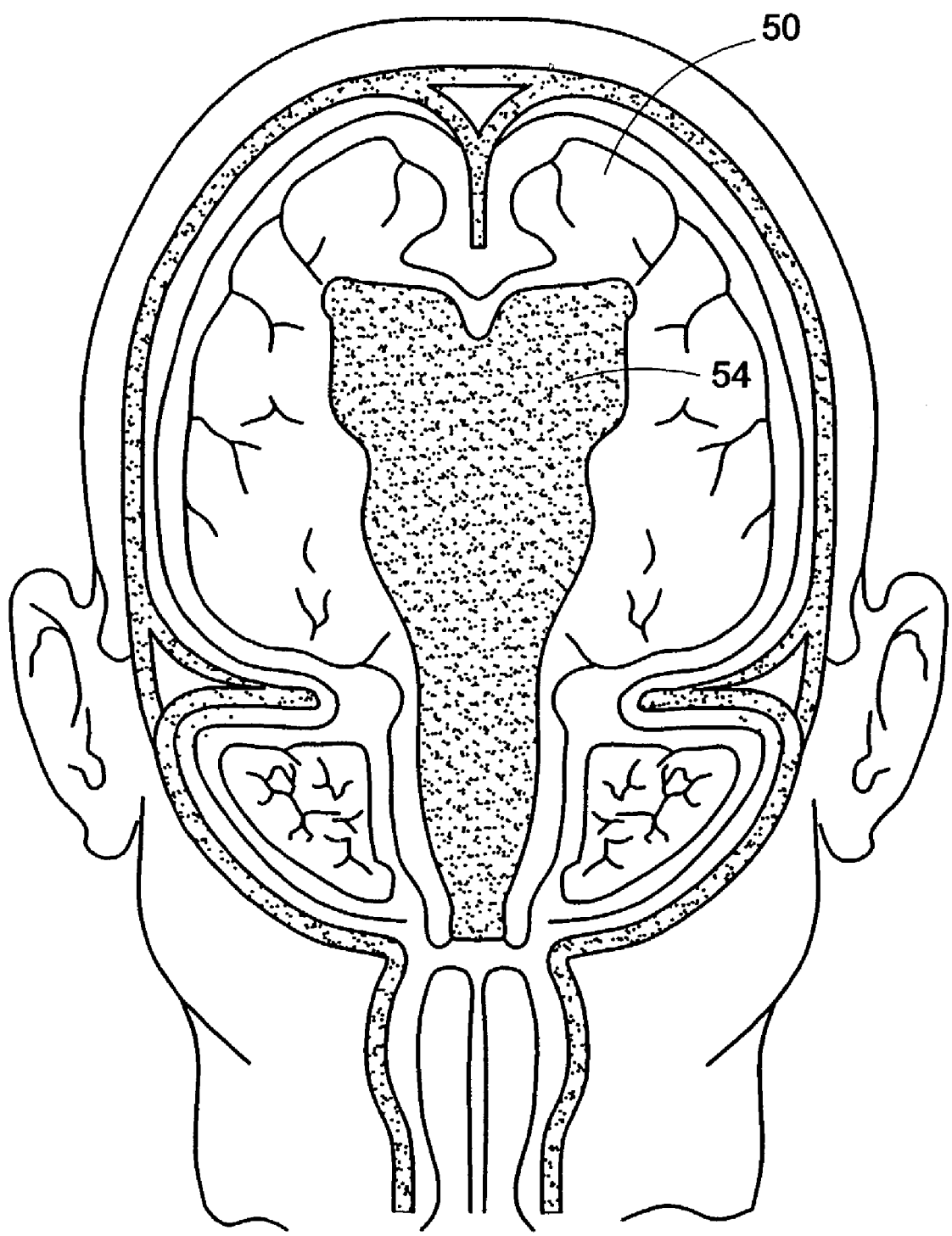
FIG. 4 is a schematic diagram of an axial scan of a hydrocephalic brain.

If the target marker 18 is projected transversely into a brain 50 (FIG. 3), the target marker 18 intersects a cerebral ventricle 54 of the brain 50. For a frontal horn ventriculostomy, the angle measured between the perpendicular reference marker 17 and the target marker 18 (angle β, FIG. 2) is approximately 35° to 55°, or approximately 125° to 145° between the anatomical reference marker 16 and the target marker 18 (angle α). Once the target has been isolated in the sagittal plane, then the target is isolated in the transverse plane. As shown in FIG. 4, the lateral ventricles extend from near the midline sagittal plane laterally toward the sides of the brain. The ventricles 54 may be located by projecting a line that intersects the midline sagittal plane about 5 to 6 cm below the inner table of the skull.

The guides 30 (FIG. 2) are oriented to direct an instrument into the brain such that the instrument would intersect the midline sagittal plane at a depth of approximately 5 to 6 cm from the inner table of the skull. This direction in the transverse plane intersects the frontal horn of the lateral ventricle (cornu anterius) of the brain. The frame 12 is then locked in place, and the annular guides are used to direct a catheter or probe toward a target, such as the frontal horn of the lateral ventricle of the brain. While this example has explained a frontal horn ventriculostomy, it should be particularly understood that a similar procedure may be used to perform lateral ventricle body, posterior (occipital) and inferior horn, and third and fourth ventriculostomies, and further understood that this method may be used to identify other targets of the brain for other procedures For example, enlargement of angle β to approximately 85° to 95° would result in preferential targeting of the atrium of the lateral ventricle (enlarged region at the junction of the body, temporal and occipital horns of the lateral ventricle).

Figure 5:
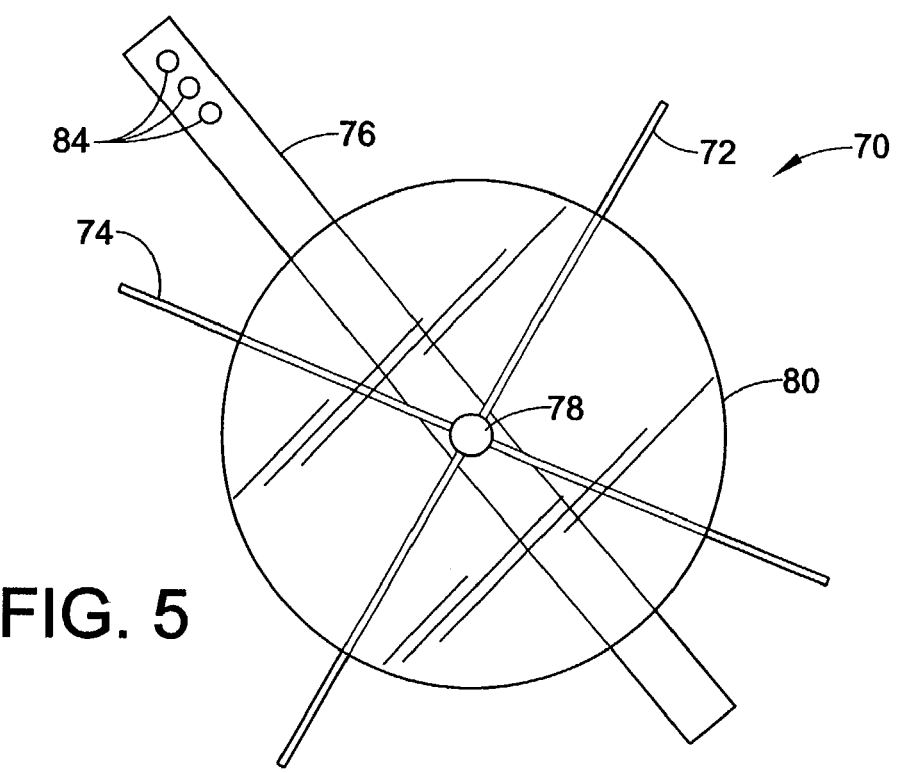
FIG. 5 is a schematic diagram of a second embodiment of a localizing device for ventriculostomy.

Referring now to FIG. 5, a lateral view of another embodiment of a localizing device 70 for ventriculostomy is shown. The localizing device 70 includes markers 72, 74, 76, a rotational frame or probe 78, and a protractor 80. The probe 78 is disposed relative to an anatomical reference point by adhesive, elastic band, surgical tape and the like. The markers 72, 74, 76, and the protractor 80 are angularly positionable about the probe 78. The markers 72, 74, and 76 rotate about an axis 19'. The markers 72, 74, 76 are relatively positionable with respect to the probe 78 so that a neurosurgeon or user may reference certain points or targets such as a portion of the brain being isolated for a procedure. The protractor 80 is oriented relative to the markers 72, 74, 76 to enable measurement of angles between the markers. When the markers 72, 74, 76 are positioned by the surgeon, the frame the target marker 76 localizes the target portion of the brain in the sagittal plane.

Figure 6:
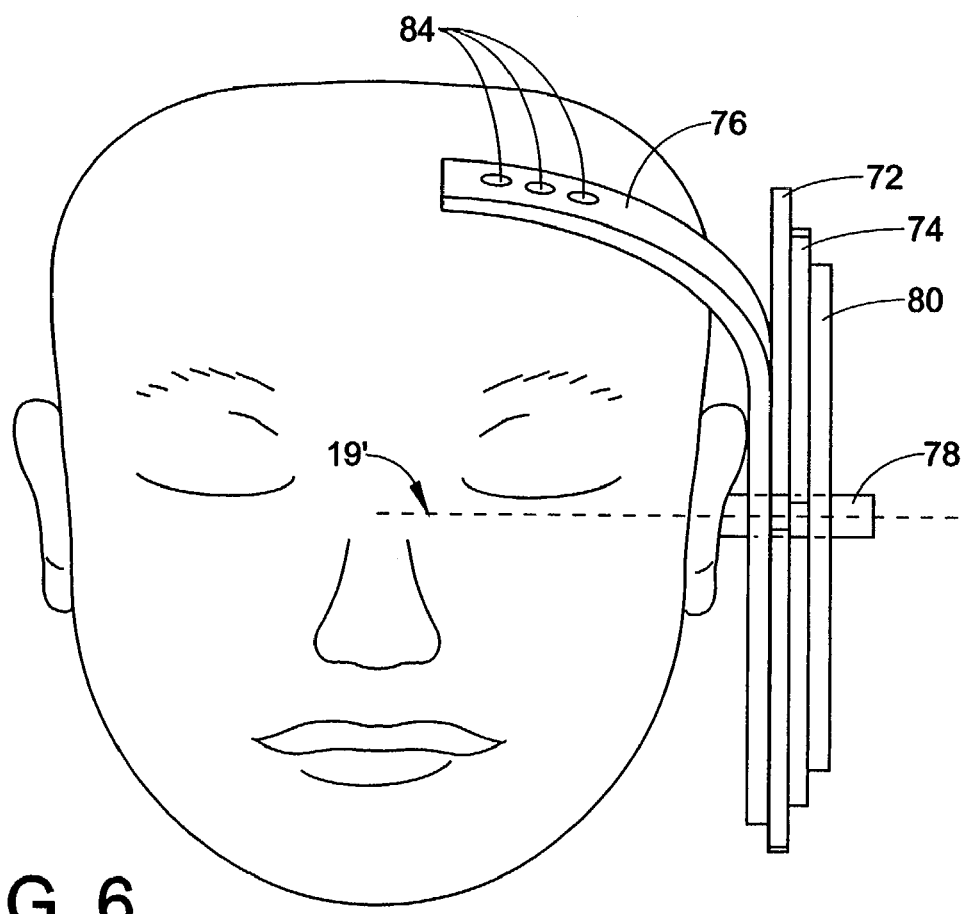
FIG. 6 is a front view of the second embodiment of FIG. 4 donned by a patient.

As best illustrated by the embodiment in FIG. 6, the target marker 76 may be made of a bendable material or otherwise angularly deformable material. The target marker 76 may also include a number of guides 84 extending through the target marker 76. The guides 84 are positioned along the target marker 76 such that a mark made on the surface of the head intersects a ventricle when a perpendicular path from the surface of the head is followed from the mark. Once the cerebral ventricle of the brain is isolated in the sagittal plane, then the target marker 76 may be bent across the surface of the head to locate the targeted portion of the brain in the transverse plane (the ideal point on the surface of the head for canulation of the ventricle).

There have been described and illustrated herein embodiments of the apparatus and method of the present invention. While in accordance with the patent statutes, a preferred embodiment has been presented, it is not intended that the scope of the invention be limited thereto. It is intended that the invention be as broad in scope as the art will allow and that the specification be read likewise. For example, those skilled in the art will appreciate that certain features of one embodiment may be combined with features of another embodiment to provide yet additional embodiments. It will therefore be appreciated by those skilled in the art that other modifications could be made to the provided invention without deviating from its spirit and scope as so claimed and described.

The invention claimed is:

1. A localizing apparatus comprising:
    a frame;
    a first portion of the frame fixable to a first anatomical reference point;
    a linear reference marker rotatable about the first anatomical reference point to align a second anatomical reference point with the first anatomical reference point;
    a target marker rotatable about the first anatomical reference point to establish a non-zero angle from the linear reference marker such that the target marker is located in a desired plane; and
    a guide configured to direct an instrument.

2. The apparatus of claim 1 wherein the first anatomical reference point includes an external auditory meatus.

3. The apparatus of claim 1 wherein the second anatomical reference point includes a mandibular angulus mandibulae.

4. The apparatus of claim 1 wherein the frame is configured to extend around a head and includes a second portion fixable to a third anatomical reference point opposite the first anatomical reference point.

5. The apparatus of claim 4 wherein the frame is disposed normal to the midline sagittal plane of a head.

6. The apparatus of claim 4 wherein the frame is configured to rotate to the target marker.

7. The apparatus of claim 1 wherein the apparatus comprises a set of annular guides extending laterally away from the midline sagittal plane.

8. The apparatus of claim 1 wherein the target marker is configured to measure an angle to a cerebral ventricle.

9. The apparatus of claim 1 wherein the target marker bends to overlie a desired target area.

10. An apparatus to position at least one instrument within a target, comprising:
    a probe configured to attach to a first reference point;
    a reference marker configured to rotate about the center axis of the probe including an end configured to align a second reference point with the first reference point;
    a target marker configured to rotate about the center axis and to be positioned at an angle such that the target marker is located in a plane that transversely passes through the target; and
    an angular measurement mechanism configured to position the target marker at the angle.

11. The apparatus of claim 10 wherein the target includes a ventricle of a human brain.

12. The apparatus of claim 10 wherein the angular measurement mechanism is fixed to the reference marker.

13. The apparatus of claim 10 wherein the target marker is positioned relative to the reference marker at an angle between 125° and 145°.

14. The apparatus of claim 10 wherein the probe is attached to the reference point by adhesive.

15. The apparatus of claim 10 wherein the target marker is configured to bend to a contour.

16. The apparatus of claim 15 wherein the target marker is further configured with guides to mark a position.

17. The apparatus of claim 10 further comprising a perpendicular reference marker disposed in a perpendicular relationship to the reference marker.

18. A localizing apparatus comprising:
    a frame configured to extend in an arc around a head, the frame having an outer diameter surface and an inner diameter surface;
    a guide extending from the outer diameter surface to the inner diameter surface, the guide being configured to direct an instrument perpendicularly toward the surface of the head;
    a first end of the frame configured to fix the frame to a first anatomical reference point;
    a second end of the frame configured to fix the frame to a second anatomical reference point;
    a reference marker configured to rotate about the first end and to align a third anatomical reference point with the first anatomical reference point; and
    a target marker configured to rotate about the first end and to be positioned at an angle from the reference marker such that the target marker is located in a plane that passes through a desired portion of the head.

* * * * *